(12) United States Patent  
Howlett et al.

(10) Patent No.: US 6,913,465 B2
(45) Date of Patent: Jul. 5, 2005

(54) DENTAL IMPLANT DELIVERY SYSTEM

(75) Inventors: Charles W. Howlett, Laguna Beach, CA (US); Grant Bullis, Corona, CA (US); Angel Bernardo, Fountain Valley, CA (US)

(73) Assignee: Nobel Biocare Services AG, Glattbrug (CH)

( * ) Notice: Subject to any disclaimer, the term of this patent is extended or adjusted under 35 U.S.C. 154(b) by 0 days.

(21) Appl. No.: 10/341,547

(22) Filed: Jan. 13, 2003

(65) Prior Publication Data

US 2004/0043358 A1 Mar. 4, 2004

Related U.S. Application Data

(60) Provisional application No. 60/347,729, filed on Jan. 11, 2002.

(51) Int. Cl.[7] ................................................. A61C 8/00
(52) U.S. Cl. ...................................... 433/173; 206/63.5
(58) Field of Search ................................. 433/172, 173, 433/174, 175, 176; 206/63.5

(56) References Cited

U.S. PATENT DOCUMENTS

| 2,347,567 | A | 4/1944 | Kresse |
| 3,346,135 | A | 10/1967 | Haitsch |
| 3,481,712 | A | 12/1969 | Bersnstein et al. |
| 4,158,256 | A | 6/1979 | Wiland et al. |
| 4,187,609 | A | 2/1980 | Edelman |
| D275,320 | S | 8/1984 | Halcomb, III et al. |
| 4,465,463 | A | 8/1984 | Hison Olde |
| 4,553,942 | A | 11/1985 | Sutter |
| 4,600,388 | A | 7/1986 | Linkow |
| 4,722,688 | A | 2/1988 | Lonca |
| 4,763,788 | A | 8/1988 | Jörnéus et al. |
| 4,856,648 | A | 8/1989 | Krueger |
| 4,856,994 | A | 8/1989 | Lazzara et al. |

(Continued)

FOREIGN PATENT DOCUMENTS

| CA | 2232009 | 6/1997 |
| EP | 0 630 621 A1 | 12/1994 |
| WO | WO 96/25895 | 6/1996 |
| WO | WO 97/20518 | 6/1997 |
| WO | WO 98/52490 | 11/1998 |
| WO | WO 98/53755 | 12/1998 |
| WO | US 03/00912 | 1/2003 |

Primary Examiner—Cary E. O'Connor
(74) Attorney, Agent, or Firm—Knobbe, Martens, Olson & Bear, LLP

(57) ABSTRACT

An assembly for securing a dental implant assembly within a package. The assembly comprises a collet that includes at least one lever arm, which defines at least in part, an angular surface and an opening for receiving the dental implant assembly. The assembly also includes a vial that defines a cavity in which the collet is positioned and a complementary angular surface that is configured such that, when the complementary angular surface moves with respect to the collet, the complementary angular surface pushes on the angular surface so as to reduce the diameter of the opening.

20 Claims, 9 Drawing Sheets

U.S. PATENT DOCUMENTS

| | | | | |
|---|---|---|---|---|
| 4,955,811 | A | 9/1990 | Lazzara et al. | |
| 5,013,242 | A | 5/1991 | Prezmecky | |
| 5,030,096 | A | 7/1991 | Hurson et al. | |
| 5,062,800 | A | 11/1991 | Niznick | 433/229 |
| 5,100,323 | A | 3/1992 | Friedman et al. | |
| 5,105,690 | A | 4/1992 | Lazzara et al. | |
| 5,108,288 | A | 4/1992 | Perry | |
| 5,158,458 | A | 10/1992 | Perry | |
| 5,213,500 | A | 5/1993 | Salazar et al. | |
| 5,254,005 | A | 10/1993 | Zuest | |
| 5,290,171 | A | 3/1994 | Daftary et al. | |
| 5,297,561 | A | 3/1994 | Hulon | |
| 5,302,125 | A | 4/1994 | Kownacki et al. | |
| 5,306,309 | A | 4/1994 | Wagner et al. | |
| 5,312,254 | A | 5/1994 | Rosenlicht | |
| 5,322,443 | A | 6/1994 | Beaty | 433/141 |
| 5,338,196 | A | 8/1994 | Beaty et al. | |
| 5,368,160 | A | 11/1994 | Leuschen et al. | 206/339 |
| 5,368,483 | A | 11/1994 | Sutter et al. | |
| 5,407,066 | A | 4/1995 | Grange | |
| 5,417,570 | A | 5/1995 | Zuest et al. | |
| 5,433,330 | A | 7/1995 | Yatsko et al. | |
| 5,437,550 | A | 8/1995 | Beaty et al. | |
| 5,453,010 | A | 9/1995 | Klein | |
| 5,462,436 | A | 10/1995 | Beaty | 433/141 |
| 5,507,463 | A | 4/1996 | Kobylinski et al. | |
| 5,525,314 | A | 6/1996 | Hurson | |
| 5,538,428 | A | 7/1996 | Staubli | 433/173 |
| 5,558,230 | A | 9/1996 | Fischer et al. | 206/570 |
| 5,564,924 | A | 10/1996 | Kwan | |
| 5,569,037 | A | 10/1996 | Moy et al. | |
| 5,582,299 | A | 12/1996 | Lazzara et al. | |
| 5,622,500 | A | 4/1997 | Niznizk | 433/173 |
| 5,636,991 | A | 6/1997 | Mays | |
| 5,651,675 | A | 7/1997 | Singer | |
| 5,683,464 | A | 11/1997 | Wagner et al. | |
| 5,692,904 | A | 12/1997 | Beaty et al. | |
| 5,733,124 | A | 3/1998 | Kwan | |
| 5,755,575 | A | 5/1998 | Biggs | 433/173 |
| 5,887,707 | A | 3/1999 | Anascavage et al. | |
| 5,904,483 | A | 5/1999 | Wade | |
| 5,961,330 | A | 10/1999 | Hanson | 433/173 |
| 5,964,591 | A | 10/1999 | Beaty et al. | 433/173 |
| 5,967,305 | A | 10/1999 | Blonder et al. | |
| 5,979,643 | A | 11/1999 | Blonder et al. | 206/63.5 |
| 5,996,779 | A | 12/1999 | Klardie et al. | 206/63.5 |
| 6,076,660 | A | 6/2000 | Day | |
| 6,203,323 | B1 | 3/2001 | Beaty et al. | 433/173 |
| 6,217,332 | B1 * | 4/2001 | Kumar | 433/173 |
| 6,247,932 | B1 * | 6/2001 | Sutter | 433/173 |
| 6,261,097 | B1 | 7/2001 | Schmutz et al. | |
| 6,280,192 | B1 * | 8/2001 | Groll et al. | 433/173 |
| D470,235 | S | 2/2003 | Kumar | |
| 6,619,958 | B2 | 9/2003 | Beaty et al. | |
| 6,626,911 | B1 | 9/2003 | Engman et al. | |
| 6,652,765 | B1 | 11/2003 | Beaty | |
| 2003/0221977 | A1 * | 12/2003 | Kumar et al. | 206/63.5 |

* cited by examiner

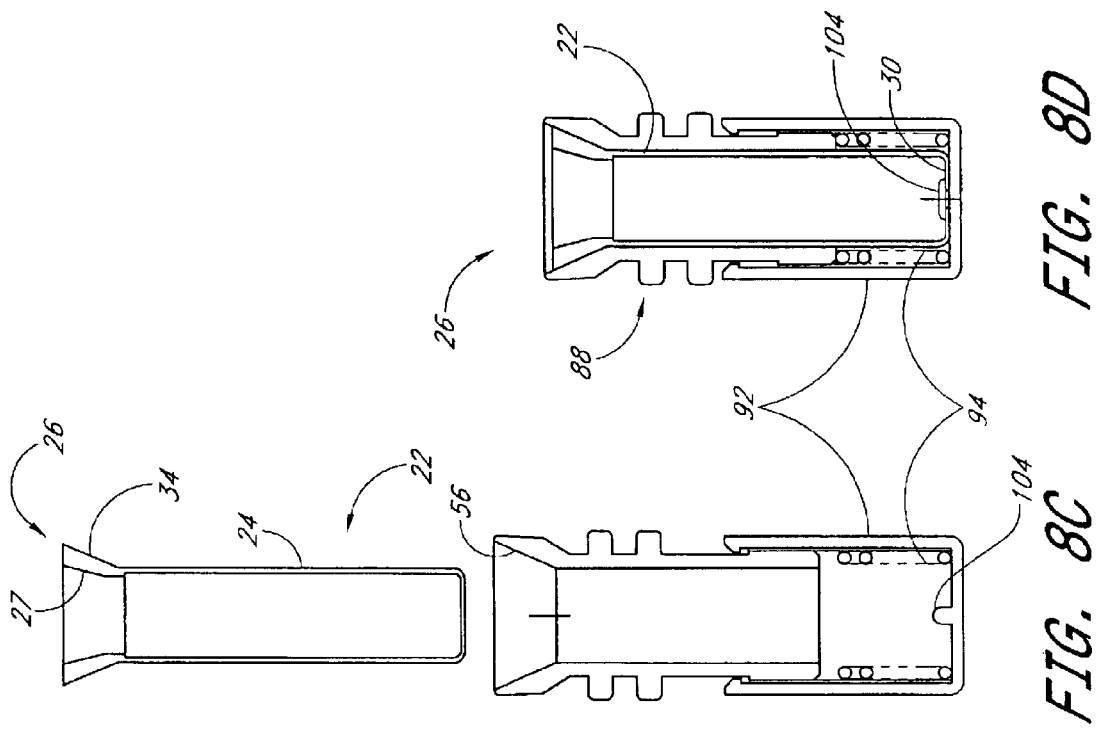
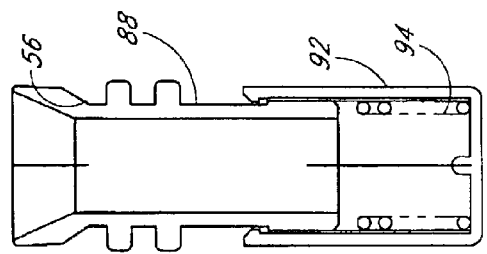
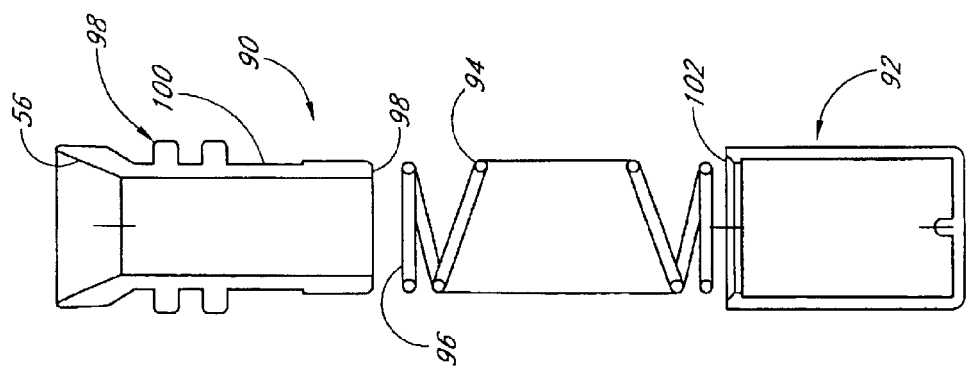
FIG. 8A  FIG. 8B  FIG. 8C  FIG. 8D

DENTAL IMPLANT DELIVERY SYSTEM

Priority Information

This application claims the priority benefit under 35 U.S.C. §119(e) of Provisional Application 60/347,729 filed Jan. 11, 2002, which is hereby incorporated by reference herein.

BACKGROUND OF THE INVENTION

1. Field of the Invention

The present invention relates generally to dental implants and, more particularly, to a dental implant delivery system.

2. Description of the Related Art

Dental implants are placed in the jaw to provide support for a dental restoration, fixed bridge or removable partial denture. Dental implants provide good chewing function and also improve the patient's cosmetic appearance thereby allowing the patient to smile, speak, and interact with others with greater confidence.

One type of dental implant widely used in the industry is typically referred to as a "threaded" implant. Threaded implants have an externally threaded body portion which is screwed into a pre-drilled hole (i.e. an osteotomy) in the patient's upper or lower jawbone. Typically, the threaded implant body is formed with a central threaded socket accessible through the overlying gum tissue for receiving and supporting one or more dental attachments or components. Types of attachments and components that are received by the central socket include healing caps, impression copings and abutments. In turn, some of these attachments and components are useful to fabricate and/or support the prosthodontic restoration.

Dental implants are typically packaged as an assembly including all the tools necessary for the insertion of the implant into an osteotomy formed in the jaw. A typical threaded implant assembly includes a threaded implant body, an implant carrier, an insertion post, a coupling screw and a healing cap. Conventionally, these components are sterilized, pre-assembled and packaged in a sterile vial. The implant carrier, insertion post, and coupling screw are tools which are used during the insertion of the implant body. Typically, the implant carrier, insertion post, coupling screw and vial are discarded after the implant body has been inserted into the osteotomy. The healing cap seals and protects the central socket of the implant body during the initial healing period, and then is discarded.

During the insertion of a conventional threaded implant, the insertion post is mechanically coupled to the top of the implant body by a coupling screw which traverses a central through-cavity in the insertion post and is threaded into the central threaded socket in the implant body. Typically, the bottom end of the insertion post is formed with a hexagonal cavity that irrotationally mates with a corresponding hexagonal protrusion formed on the top of the implant body thereby preventing any relative rotation between the insertion post and implant body while coupled.

An implant carrier is releasably coupled to the top of the insertion post and provides the dental practitioner with a means to grip and manipulate the assembly during the initial implantation procedure. Typically, the implant carrier is formed with a generally hexagonal internal passage at its bottom end which mates with a generally hexagonal outer surface near the top of the insertion post. The dental practitioner uses the implant carrier to manipulate the implant body into the proper location within the jawbone. Torque is applied to the implant carrier which is transferred, via the insertion post, to the threaded implant body.

In use, the first step of a typical implantation procedure involves making an incision in the patient's gum tissue. A portion of the gum tissue is then folded back and an osteotomy is drilled in the jawbone. The diameter of the osteotomy is equal to or slightly smaller than the diameter of the implant body. The implant carrier is then used to transport the threaded implant assembly to the surgical site. The implant carrier is gripped by the practitioner and is used to manipulate the implant body into the correct position and then to partially screw the threaded implant body into the osteotomy.

Once the implant body has been initially placed in the osteotomy and tightened manually, the implant carrier is decoupled from the insertion post and is removed from the surgical site. If necessary, a suitable wrench or dental hand piece is then used to engage the insertion post and drive the implant to its final depth within the osteotomy. The coupling screw is then removed and the insertion post is decoupled from the implant body leaving only the implant body in the patient's mouth.

The healing cap is housed in a cavity formed in the top of the implant carrier where it is contained by a paper barrier until needed. At this point, the healing cap is removed from the implant carrier and is threaded into the central socket of the implant body. Typically, a tool with a hexagonal tip is inserted into a corresponding mating hexagonal recess located in the top center of the healing cap and is used to apply torque to tighten the healing cap. The healing cap protects the implant socket against bone or tissue ingrowth during the initial healing period, and also prevents the entry of bacteria or other contaminants into the central socket of the implant body.

The insertion of the implant body and healing cap is then followed by an initial healing period in which the bone is allowed to surround and retain the implant (i.e. "osseointegrate" with the implant) and the gum tissue is allowed to heal over the implant body and healing cap. For implants placed in the mandible, healing typically requires about three months; for implants in the maxilla, the healing period typically requires about six months.

After the implant body has sufficiently osseointegrated with the jawbone, the gum tissue is re-opened by making an incision and the gum tissue is folded back to expose the healing cap. A hexagonal tool is inserted into the recess in the top of the healing cap and torque is applied to rotate the healing cap out of the implant socket and to remove it from the implant body. During this step of the procedure, great care must be used to remove the healing cap without disturbing the position of the implant body. Any disturbance of the implant body during the removal of the healing cap could damage the osseointegration between the implant body and the jawbone. Damage to the osseointegration is very undesirable and could endanger the entire restoration process by destabilizing the implant. In addition, any movement of the implant body could result in gaps or spaces between the implant body and jawbone which could in turn lead to infection by bacteria and/or other contaminants.

After the healing cap has been unscrewed and removed from the patient's mouth, a suitable healing abutment is inserted into the central socket. The healing abutment extends through the gum tissue overlying the implant site. A second healing period then ensues in which the gum tissue is allowed to heal around the post-osseointegration healing abutment. Typically, this second healing period lasts from four to eight weeks.

After the second healing period has ended, the healing abutment is removed from the implant body. Typically, an impression is taken of the patient's mouth to fabricate a prosthesis or dental restoration. An abutment supporting the final restoration is then attached to the implant body. Lastly, the restoration is cemented or screwed to the abutment and/or implant body to complete the placement of the prosthodontic restoration in the patient's mouth.

SUMMARY OF THE INVENTION

The procedures and devices described above for installing a dental implant are commonly used by dental practitioners. However, these procedures and devices suffer from several significant shortcomings. For example, as mentioned above, the dental implant is typically packaged within a sterile vial, which typically includes a bore in which the dental implant rests. In some arrangements, the bore usually includes a retention member, such as a slanted shelf, which supports the dental implant and prevents it from falling into the lower portions of the sterile vial. However, this arrangement is generally undesirable because if the vial is overturned the dental implant can fall out of the vial and become damaged or contaminated. In other arrangements, the bore includes an O-ring that causes resistant constriction of the size of the bore so as to exert a constant pressure against the implant, which secures the implant within the vial. This arrangement is generally undesirable because the constant pressure of the O-ring may cause the dental carrier to disengage from the implant when the implant is withdrawn from the vial.

Dental implants come in various sizes. For example, the diameter of dental implants typically lie within the range of approximately three to six millimeters. In a similar manner, the length of the dental implant also varies. It would be advantageous if a single dental implant packaging system could accommodate various sizes of dental implant with little or no modifications.

Therefore, one embodiment of the present invention comprises an assembly for securing a dental implant assembly within a package. The assembly comprises a collet, a member and a spacer. The collet has an open end for receiving the dental implant assembly and a distal end. The collet comprises at least one lever arm, which defines at least in part, a mating surface. The member comprises a complementary mating surface. The member and the collet are moveable with respect to each other such that the complementary mating surface can engage the mating surface so as to selectively compress the open end of the collet about the dental implant assembly. The spacer is configured to position the dental implant assembly within the collet.

Another embodiment of the invention comprises a dental implant assembly. The dental implant assembly comprises a container for the implant assembly, having at least one open end. At least one retention surface is carried by the container. The retention surface movable between a first position in which it engages a dental implant positioned within the container and a second position in which is disengaged from the implant, to allow the implant to be removed from the container.

Another embodiment of the invention comprises a dental implant assembly storage system. The system comprises a sterile vial and a holder. The holder is positioned within the sterile vial and has a retention surface for engaging the implant assembly. The holder also includes means for moving the retention surface between a first position in which it engages a dental implant and a second position in which it is disengaged from the dental implant, to allow the dental implant to be removed from the holder.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed herein.

BRIEF DESCRIPTION OF THE DRAWINGS

These and other features, aspects and advantages of the present invention will now be described with reference to the drawings of a preferred embodiment, which embodiment is intended to illustrate and not to limit the invention, and in which figures:

FIGS. 8A–D illustrate an actuator, a spring, a base and a collet of the packaging system of FIG. 6 being assembled together.

DETAILED DESCRIPTION OF THE PREFERRED EMBODIMENT

Figure 1A:
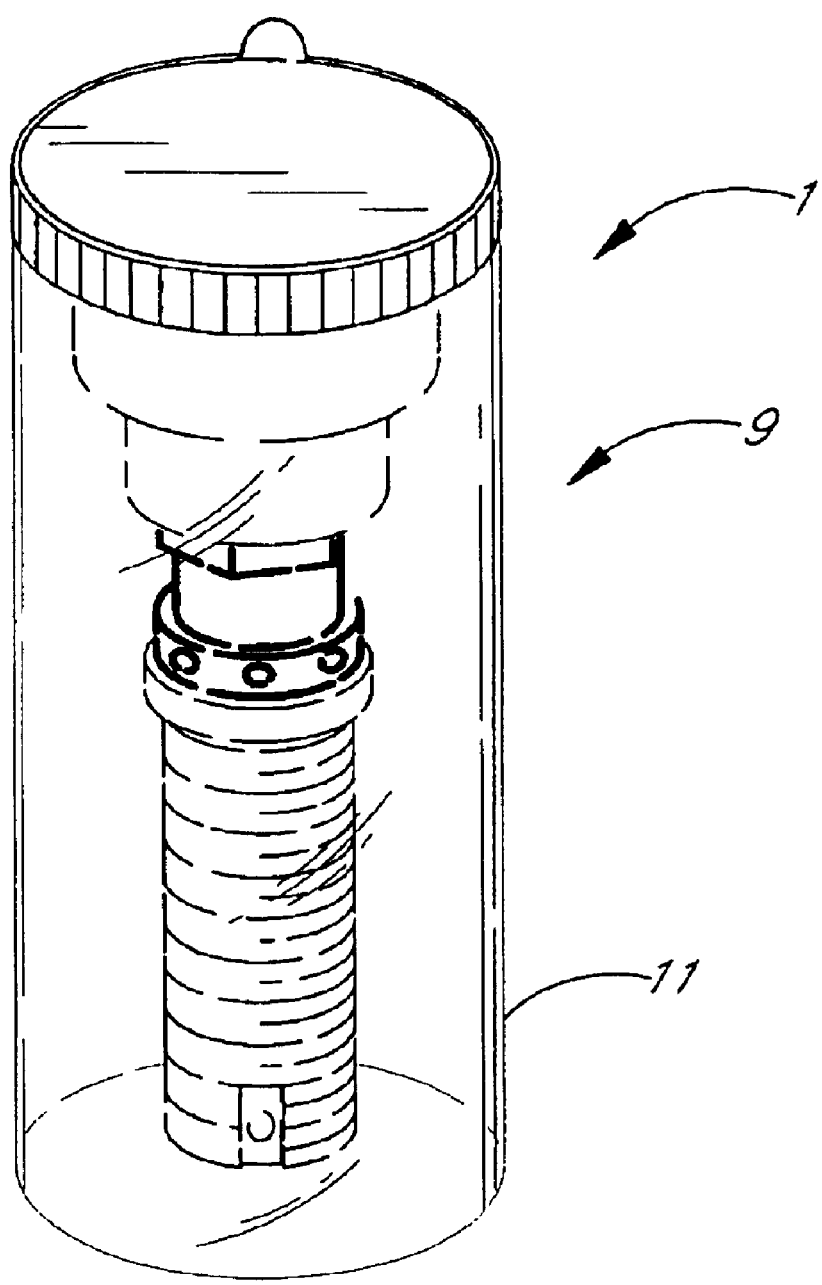
FIG. 1A is a perspective view of a conventional threaded dental implant assembly packaged in a sterile vial in accordance with the prior art.
Figure 1B:
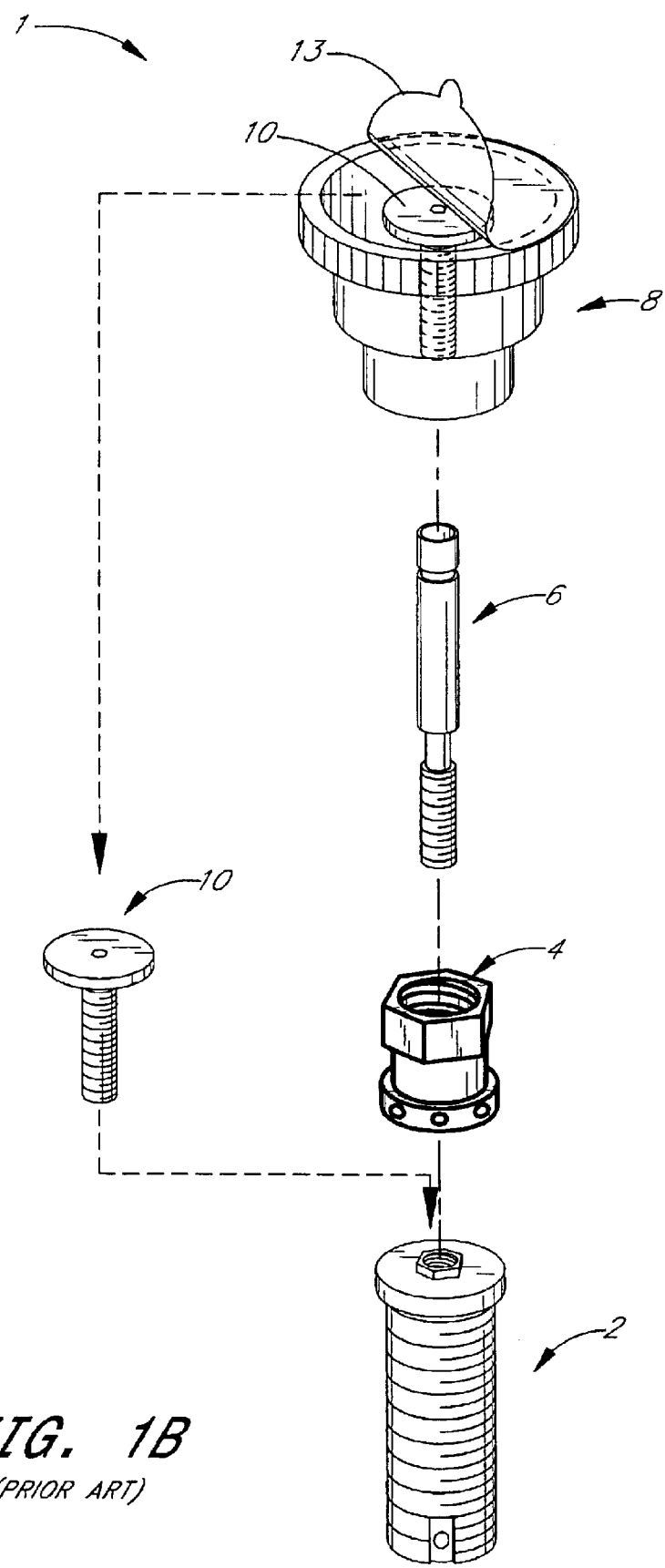
FIG. 1B is an exploded view of the conventional threaded dental implant assembly.

The insertion of a conventional threaded implant body into an osteotomy formed in a jawbone is a difficult and time consuming procedure. As shown in FIGS. 1A and 1B, a conventional implant assembly 1 and delivery system typically includes an implant 2, an insertion post 4 coupled to the implant 2 by a coupling screw 6, an implant carrier 8 coupled to the insertion post 4, and a healing cap 10. Conventionally, these components are sterilized, preassembled and packaged within a sterile vial 9 (see FIG. 1A). The illustrated vial 9 comprises a lower portion 11, which is removably attached to the implant carrier 8.

In use, the dental practitioner drills a hole (i.e. an osteotomy) in the patient's jawbone. The dental practitioner then grips the implant carrier 8 and removes the implant assembly from the vial 9. He or she then transports the implant assembly 1 to the surgical site, and manipulates the implant body 2 into position over the osteotomy. Once the implant body 2 is properly positioned, the dental practitioner applies torque to the implant carrier 8 to begin screwing the implant body into the osteotomy. If necessary, the implant carrier 8 is then decoupled from the insertion post 4 and a tool, such as a dental handpiece or driver, is attached to the insertion post to drive the implant body the rest of the way into the osteotomy. After the implant body is properly seated, the insertion post is decoupled from the implant body by removing the coupling screw. To protect against infection, a healing cap 10 is screwed into the central socket of the implant body 2 to cover the socket during the initial healing period. The healing cap 10 is typically packaged within a hollow portion of the carrier 8 and is covered by a sterile foil 13, which can be peeled back to access the healing cap 10.

The process described above can has several drawbacks. For example, the process lacks flexibility. If the dental practitioner wishes to use a tool, such as a handpiece or wrench, to transport the implant assembly to the surgical site, the current process typically requires the additional step of removing the implant carrier before attaching the tool to the implant assembly. Furthermore, the dental practitioner typically must either insert the implant assembly into the osteotomy before removing the implant carrier or handle the implant assembly with their hands or an additional tool, which increases the risk of contamination. In addition, the implant vial and insertion post typically need to be modified to accommodate different sizes of implants.

Figure 2:
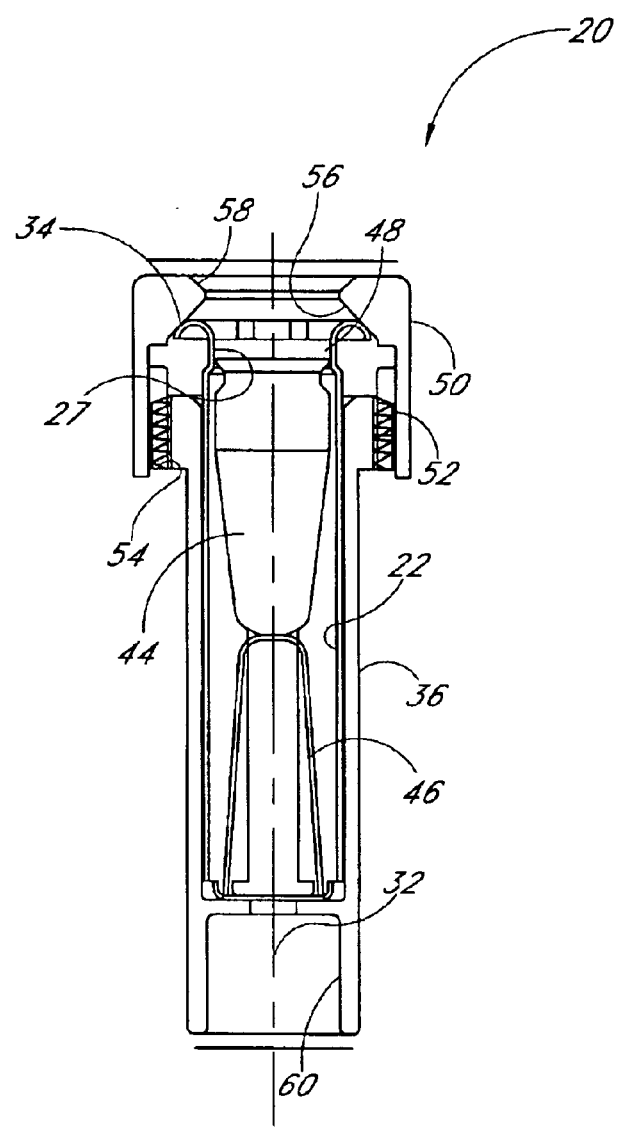
FIG. 2 is a cross-sectional view of a packaging system.
Figure 3:
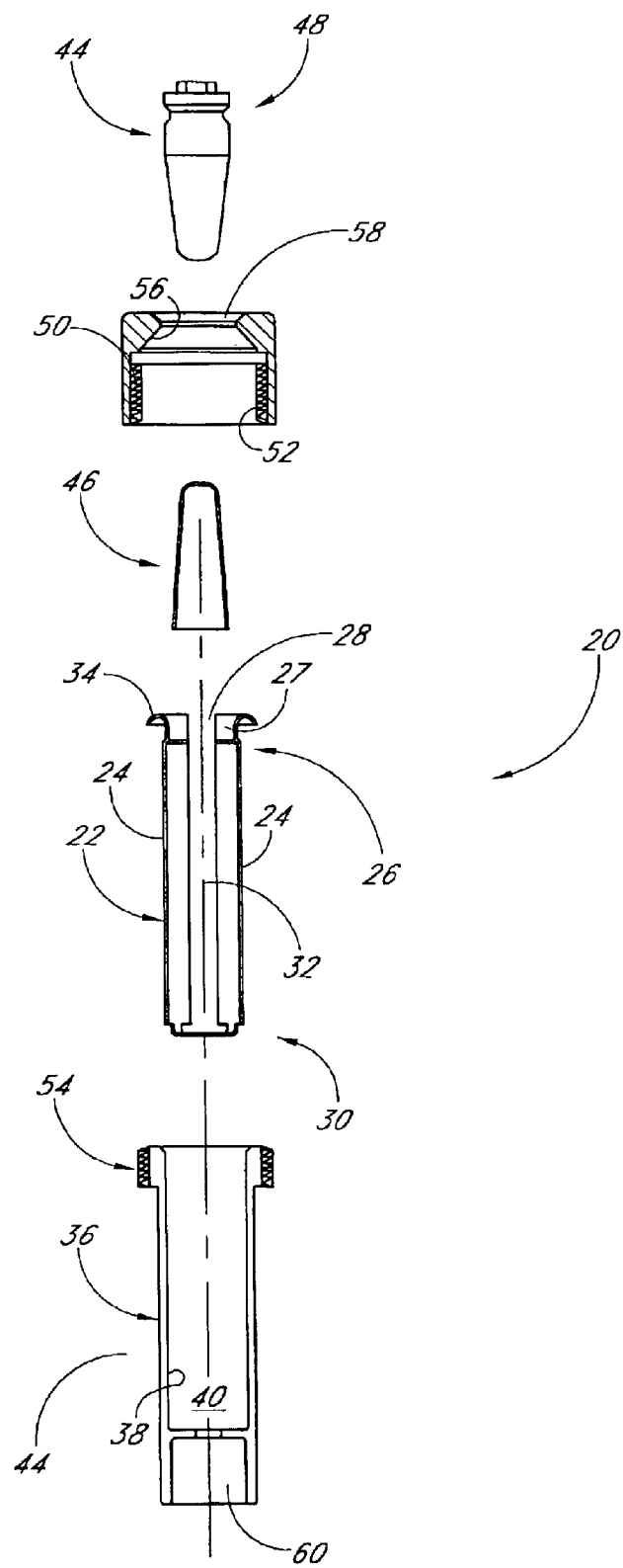
FIG. 3 is an exploded cross-sectional view of the packaging system of FIG. 2.

Reference is now made to preferred embodiments of the invention, which are illustrated in the accompanying drawings. FIGS. 2 and 3 illustrate the components of one embodiment of a packaging system 20. The packaging system 20 may be placed, for example, within a sterile outer vial such as those described above with reference to FIG. 1A, a blister pack with a lid (e.g., a Tyvek™ lid) or other suitable containers. It should also be appreciated that the packaging system 20 may be used to secure several types of implants or implant assemblies such as an implant body that is coupled to an insertion post and/or other components (see e.g., FIGS. 1A and 1B), or an implant by itself.

The packaging system 20 includes a collet 22, which comprises at least two jaws or lever arms 24. The collet 22 may be made of titanium or another suitably resilient material. In the illustrated embodiment, at a proximal or open end 26 of the collet 22, gaps 28 separate the lever arms 24. The open end 26 defines a retention surface 27, which as explained below can be moved between a first position in which it engages a dental implant positioned within the system 20 and a second position in which is disengaged from the implant, to allow the implant to be removed from the system 20. At a lower end 30, the lever arms 24 are coupled together such that at the open end 26 the retention surface 27 can be flexed towards and away from a longitudinal axis 32 of the collet 22.

The open end 26 and the retention surface 27 define an opening, the diameter of which can be reduced by deflecting the lever arms 24 towards the longitudinal axis 32. In the illustrated arrangement, the lever arms 24 are compressed by applying a force to a mating surface 34, which is preferably provided near or at the open end 26 of the lever arms 24. In the illustrated arrangement, the mating surface 34 generally slants away from the longitudinal axis 32 as it extends in the distal direction.

In the illustrated embodiment, the collet 22 is positioned within a tubular lower member 36. The lower member 36 includes an inner surface 38, which defines a cavity 40. The inner surface 38 is configured such that a lower portion of the collet 22 lies within the cavity 40. Preferably, the inner surface includes a support surface 42, which supports the collet 22 such that the open end 26 and the mating surface 34 of the collet 22 lie above the cavity 40.

As best seen in FIG. 2, the open end 26 of the lever arms 24 is configured to receive an implant 44. A spacer 46 is positioned within the collet 22 to support the implant 44 in such a manner that the retention surface 27 of the collet 22 only contacts the upper portions 48 of the implant body. In the illustrated embodiment, the retention surface 27 only contacts the smooth surfaces of the collar 48 of the implant body 12. In this manner, the collet 22 in a first position does not contact the threaded or lower portions of the implant 12, which may be threaded and/or coated with material to promote osseointegration.

In the illustrated embodiment, a proximal member 50 is used to compress the open end 26 of the collet 22. The proximal member 50 may include a threaded portion 52, which is configured to engage a corresponding threaded portion 54 formed on the proximal end of the lower member 36. The proximal member 50 also includes a complementary mating surface 56, which is configured to engage the mating surface 34 of the collet 22 as the proximal member 50 is tightened onto the lower member 36. In the illustrated embodiment, the complementary mating surface 56 slants away from the longitudinal axis 32 as it extends in the distal direction. The mating angle between the mating surface 34 of the collet 22 and the complementary mating surface 56 is preferably about 4 to 6 degrees.

As best seen in FIG. 2, the proximal member 50 is configured to fit over the open end 26 of the collet 22 and the lower member 36 such that the threaded portion 52 of the proximal member 50 can engage the threaded portion 54 of the lower member 36. Tightening the proximal member 50 moves the proximal member 50 distally with respect to the collet 22, which compresses the open end 26 of the collet 22 as the complementary mating surface 56 engages the mating surface 34 of the collet 22. Conversely, loosening the proximal member 50 moves the proximal member 50 proximally with respect to the collet 22 and allows the open end 26 to expand. In this manner, the implant body 44 can be secured within the collet 22 by tightening the proximal member 50 and released by loosening the proximal member. The implant 44 is removed from the collet 22 through an opening 58 provided in the proximal member 50.

As mentioned above, the packaging system 20 can be placed within a sterile vial. In one embodiment, the dental surgeon removes the packaging system 20 from the sterile vial. The surgeon can then loosen the proximal member 50 with one hand while holding the lower member 36 with the other hand. Once the implant 50 is released from the collet 22, the surgeon can release the proximal member 50 and grip a carrying member or a driver configured to engage the top end of the implant 44. While still holding the lower member 36, the surgeon can insert the carrying member or driver into the top end of the implant 44 and remove the implant 44 from the packaging system 20. If necessary, the surgeon can place the implant 44 back into the collet 22 and secure the implant 44 by tightening the proximal member 50.

It should be appreciated that the retention surface 27 can be configured such that in the compressed position the retention surface provides a friction or interference fit. For example, in the illustrated embodiment, the retention surface 27 contacts the collar 48 of the implant 44 in a friction fit. In a modified arrangement, the retention surface may include protrusions, which form jaws to hold the implant in an interference fit.

Figure 4:
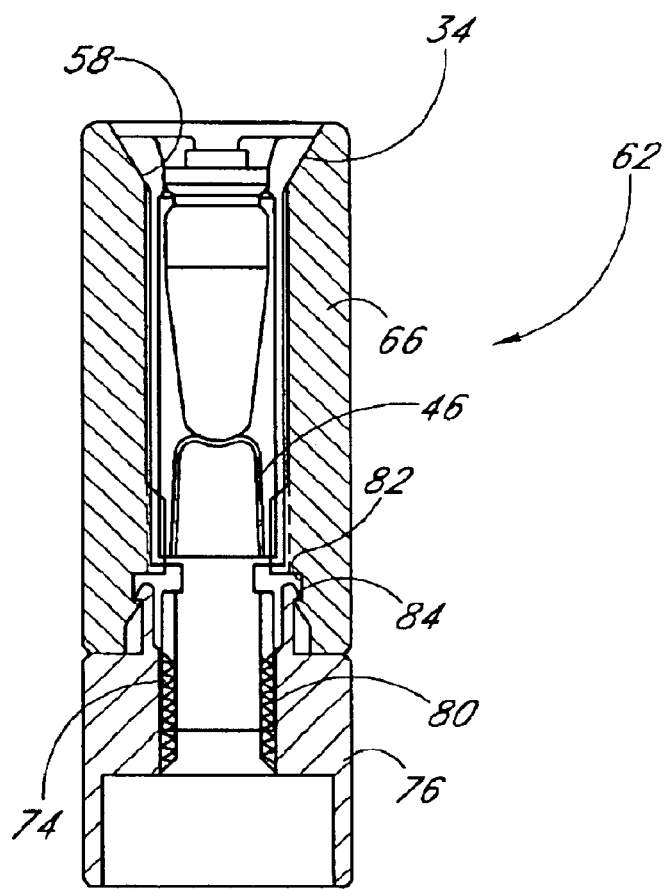
FIG. 4 is a cross-sectional view of another embodiment of a packaging system.
Figure 5:
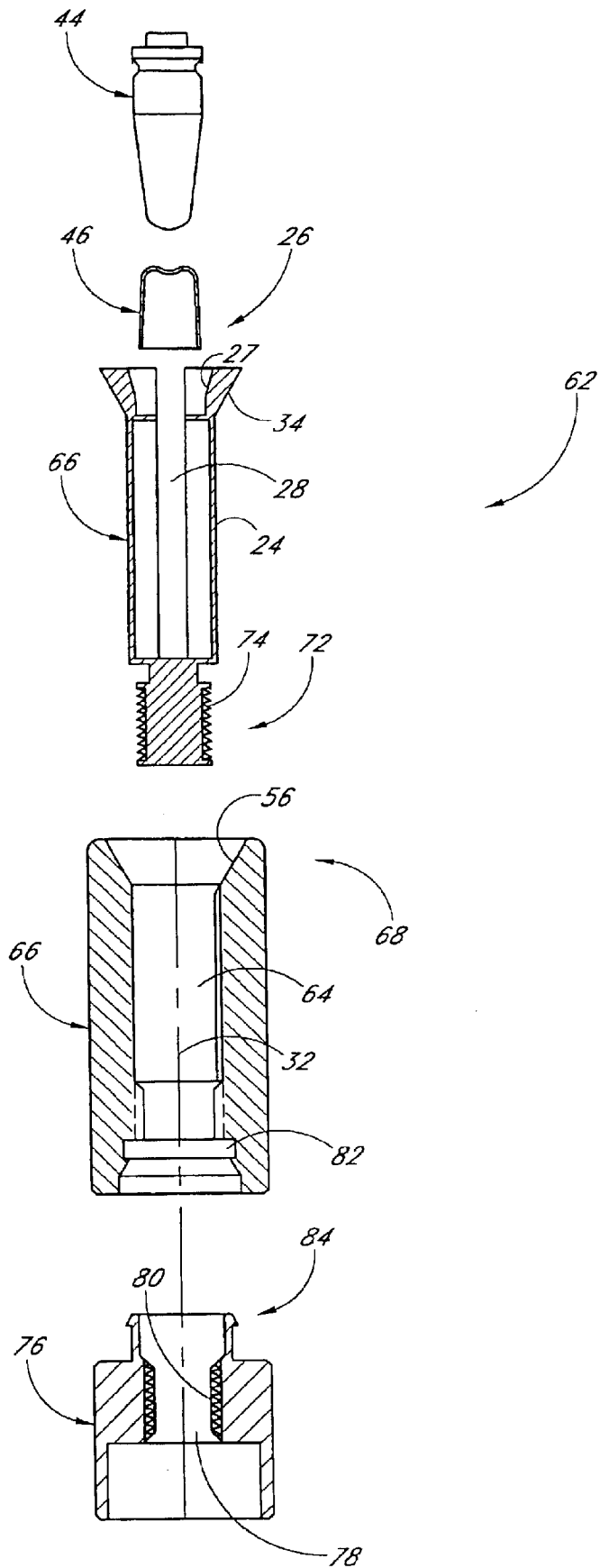
FIG. 5 is an exploded cross-sectional view of the packaging system of FIG. 4.

FIGS. 4 and 5 illustrate a modified packaging system 62 wherein like numbers are used to refer to parts similar to those of the packaging system 20 of FIGS. 2 and 3. In this embodiment, the collet 22 fits within a bore 64 (see FIG. 5) of a sleeve 66. The proximal end 68 of the sleeve 66 includes the complementary mating surface 56, which in the illustrated embodiment slants towards the longitudinal axis 32 in the distal direction. In a similar manner, in this embodiment, the mating surface 34 of the collet 22 also slants towards the longitudinal axis 32 in the distal direction. As with the previous embodiment, the mating angle between the mating surfaces 34, 56 is preferably 4 to 6 degrees.

As best seen in FIG. 4, the spacer 46 supports the implant 44 within the collet 22 such that only the upper portions of the implant 44 and preferably only the smooth surfaces of the collar of the implant 44 contact the retention surface 27.

In the illustrated embodiment, the distal end of the collet 22 includes a threaded post 72, which includes threads 74. When the collet 22 is positioned within the sleeve 66, the threaded post 72 is configured to extend through the bore 64 and to engage a distal member 76. The distal member 76 includes a bore 78 with a threaded portion 80 configured to engage the threaded post 72. Of course, in a modified embodiment, the arrangement of the threaded post 72 and threaded bore 78 may be reversed such that the distal member 76 includes a threaded post while the distal end of the collet 22 includes a threaded bore.

As best seen in FIG. 4, the bore 64 of the sleeve 66 preferably includes an annular groove 82, which is configured to receive an annular retaining ring 84 positioned on the distal member 76. The annular retaining ring 84, when positioned in the annular groove 82, couples the distal member 76 to the sleeve 66 while still permitting rotation and limited distal/proximal movement along the longitudinal axis 32 between the sleeve 66 and the distal member 66. In one embodiment, the annular retaining ring 84 is configured such that it can be inserted into the annular groove 82 by press-fitting the proximal end of the distal member 76 into the distal end of the bore 64.

In this embodiment, to compress the open end 26 of the collet 22, the distal member 76 is tightened through rotation. As the distal member 76 is tightened, the collet 22 is pulled in a distal direction. In this manner, the mating surface 34 of the collet 22 is compressed against the complementary mating surface 56 of the sleeve 66. To release the open end 26 of the collet 22, the distal member 76 is loosened so as to push the collet 22 away from the sleeve 66.

Figure 6:
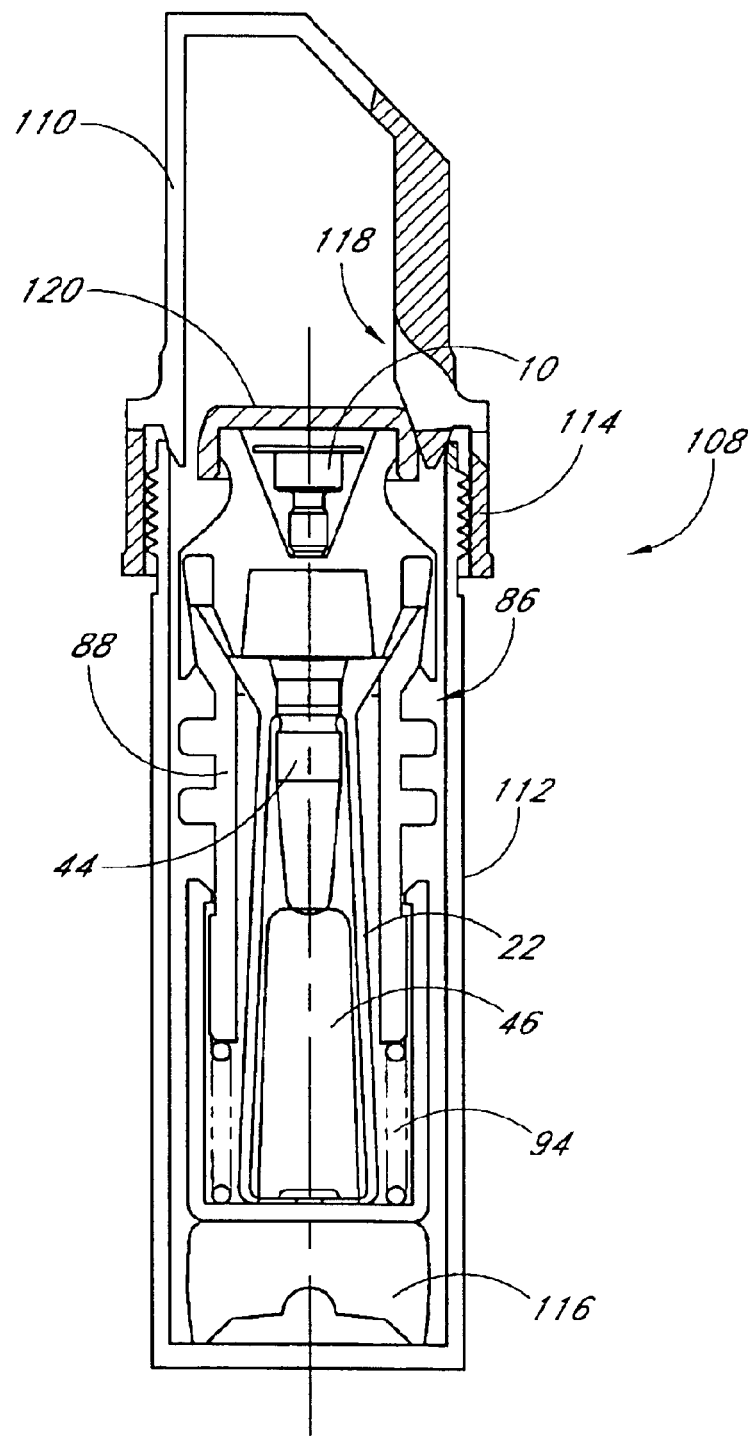
FIG. 6 is a cross-sectional view of another embodiment of a packaging system positioned within a sterile vial.

FIGS. 6–8D illustrate another modified packaging system 86 wherein like numbers are used to refer to parts similar to the packaging system 62 of FIGS. 4 and 5. FIG. 6 shows the packaging system 86 positioned in a sterile vial 108, which comprises an upper portion 110 and a lower portion 112 that are coupled together by providing complementary threads 114 on the inner surface of the upper portion 110 and outer surface of the lower portion 112. The packaging system 86 is secured within the vial 108 between a support or cushion 116 that is placed at the bottom of the lower portion of the vial 108 and a positioning member 118 formed on the upper portion 110. In this manner, when the upper portion 110 is secured to the lower portion 112, the packaging system 86 is held between the cushion 116 and the positioning member 118, thereby preventing movement within the vial 108.

Figure 7:
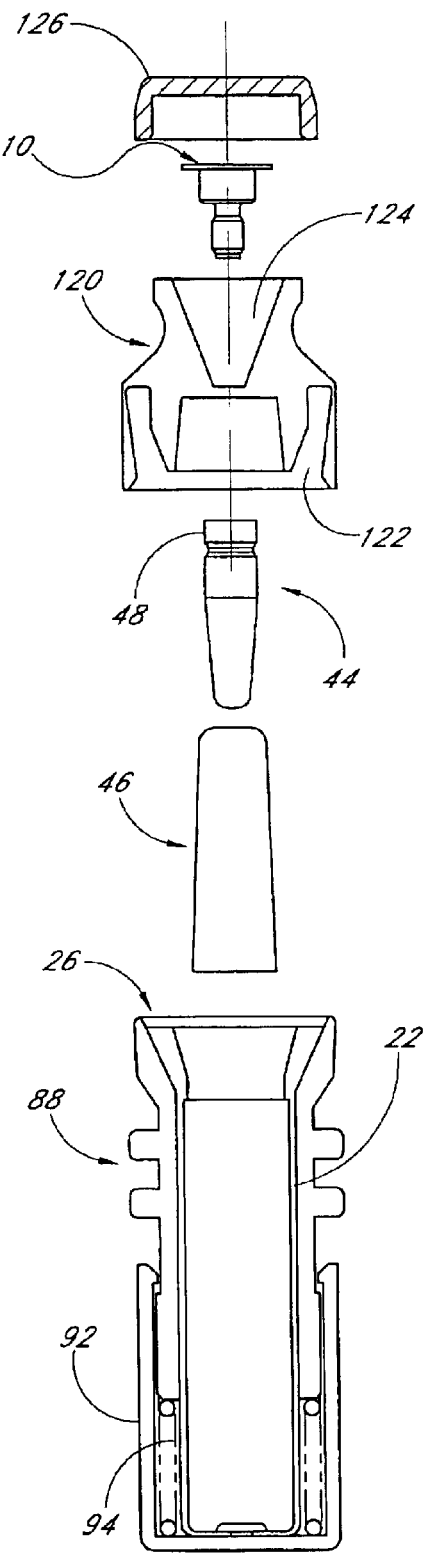
FIG. 7 is an exploded cross-sectional view the packaging system of FIG. 6.

With reference now to FIGS. 7–8D, in this embodiment, the packaging system 86 includes an actuator sleeve 88, which includes a lower portion 90 that is configured to move longitudinally within a cavity of a base 92. As best seen in FIGS. 8A and 8B, a spring 94 is positioned, in a compressed state, between the actuator 88 and base 92 such that an upper surface 96 of the spring 94 contacts a lower surface 98 of the actuator 88. In the illustrated embodiment, the actuator 88 is restrained within the base 92 by providing an annular groove 100 on the lower portion 90 of the actuator, which interacts with a lip or ridge 102 provide on the base 92. In this manner, the actuator 88 is coupled to the base 92 while still permitting limited longitudinal movement between the two parts.

As with the previous embodiment, the actuator 88 includes the complementary mating surface 56, which in the illustrated embodiment slants towards the longitudinal axis in the distal direction. Correspondingly, as best seen in FIG. 8C, the mating surface 34 on the collet 22 also slants towards the longitudinal axis in the distal direction. As with the previous embodiment, the mating angle between the mating surfaces 34, 56 is preferably about 4 to 6 degrees.

As best seen in FIG. 8D, the collet 22 is positioned within the actuator 88 and base 92. The collet 22 is preferably secured to the base 92. As such, in the illustrated arrangement, the base 92 includes a stake 104 which extend through the lower portion 30 of the collet 22. The collet 22, actuator 88 and base 92 are configured such that the mating surfaces 34, 56 are generally aligned with each other.

As with the previous embodiments, the spacer 46 is positioned within the collet 22 to support the implant 44 in such a manner that the retention surface 27 of the collet 22 only contacts the upper portions 48 of the implant. Preferably, the open end 26 only contacts the smooth surfaces of the collar 48 of the implant body 12. In this manner, the collet 22 in a compressed position does not contact the threaded or lower portions of the implant 12, which may be threaded and/or coated with material to promote osseointegration.

In this embodiment, the spring 94 is configured to push the actuator 88 proximally such that the complementary mating surface 56 compresses against the mating surface 34 of the collet 22. In this manner, the spring 94 pushes the open end 26 of the collet 22 in a secured clamped position about the collar 48 of the implant 44. To release the implant 44, the actuator 88 is pushed distally against the force of the spring 94. This moves the complementary mating surface 56 away from the mating surface 34 of the collet 22 thereby expanding the open end 26 and releasing the implant 44.

The illustrated packaging system 86 preferably also includes a cap 120 for storing the healing cap or screw 10. The illustrated cap 114 includes an annular groove 122, which is configured so that the cap 120 can be slipped onto the top end of the actuator 88 as shown in FIG. 6. The cap 120 defines a cavity 124 in which the healing cap or screw 10 can be stored. The cavity 124 is preferably closed by a removable lid 126, which can fit over the top end of the cap 120.

The utility of the present invention will be readily apparent to those skilled in the art. The implant delivery systems described above provide an improved device for securing a dental implant assembly within a sterile package. Advantageously, these embodiments are capable releasably holding dental implants of various diameters and lengths. Specifically, the open end 26 of the collet 22 can be expanded or contracted to hold implants of various diameters. Implants of various lengths can also be accommodated by providing spacers 46 of various heights. In addition, the dental implant packaging system can be configured such that the collet 22 contacts the implant only on the smooth upper surfaces, such as, the collar. This protects the lower portion of the implant from being damaged. Finally, the dental implant packaging systems also allow the physician to replace the implant into the collet if necessary.

It should be noted that certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An assembly for securing a dental implant assembly within a package, comprising:
    a collet having an open end for receiving the dental implant assembly and a distal end, the collet comprising at least one lever arm, which defines at least in part, a mating surface;
    a first member that comprises a complementary mating surface, the first member and the collet being moveable with respect to each other such that the mating surfaces interact to selectively compress the open end of the collet about the dental implant assembly; and
    a spacer configured to position the dental implant assembly within the collet.

2. The assembly as in claim 1, wherein assembly includes a lower member, which defines a cavity in which the collet is at least partially positioned.

3. The assembly as in claim 1, wherein the first member is a sleeve in which the collet is at least partially positioned.

4. The assembly as in claim 3, comprising a spring and a base member, which defines a cavity, the spring being positioned between the sleeve and a lower surface of the base member so as to bias the sleeve away from the lower surface such that the sleeve compresses the open end of the collet.

5. The assembly as in claim 1, wherein the dental assembly comprises a dental implant having a collar and the spacer is configured such that the open end of the collet only contacts the collar.

6. A dental implant assembly retention system, comprising:
    a container for the implant assembly, having at least one open end; and
    at least one retention surface carried by the container, the retention surface movable between a first position in which it engages a dental implant positioned within the container and a second position in which it is disengaged from the implant, to allow the implant to be removed from the container;
    wherein the retention surface is on a movable lever arm;
    the assembly further comprising an actuator for moving the retention surface between the first and second positions.

7. The dental implant assembly retention system as in claim 6, wherein the retention surface provides an interference fit with the implant when the retention surface is in the first position.

8. The dental implant assembly retention system as in claim 6, wherein the retention surface provides a friction fit with the implant when the retention surface is in the first position.

9. The dental implant assembly retention system as in claim 6, wherein the retention surface is moveable in a lateral direction in response to axial movement of the actuator.

10. The dental implant assembly retention system as in claim 6, wherein the retention surface is moveable in a lateral direction in response to rotation of the actuator about a longitudinal axis of the implant.

11. The dental implant assembly retention system as in claim 6, further comprising a spacer configured to position the implant within the container.

12. A dental implant assembly retention system, comprising:
    a container for the implant assembly, having at least one open end; and
    at least one retention surface carried by the container, the retention surface movable between a first position in which it engages a dental implant positioned within the container and a second position in which it is disengaged from the implant, to allow the implant to be removed from the container;
    wherein the retention surface is on a movable lever arm, further comprising a spacer configured position the implant within the container such that the retention surface only contacts a collar portion of the implant.

13. A dental implant assembly retention system, comprising:
    a container for the implant assembly, having at least one open end;
    at least one retention surface carried by the container, the retention surface movable between a first position in which it engages a dental implant positioned within the container and a second position in which it is disengaged from the implant, to allow the implant to be removed from the container; and
    an actuator for moving the retention surface between the first and second positions.

14. The dental implant assembly retention system as in claim 13, wherein the retention surface provides an interference fit with the implant when the retention surface is in the first position.

15. The dental implant assembly retention system as in claim 13, wherein the retention surface provides a friction fit with the implant when the retention surface is in the first position.

16. The dental implant assembly retention system as in claim 13, wherein the retention surface is moveable in a lateral direction in response to axial movement of the actuator.

17. The dental implant assembly retention system as in claim 13, wherein the retention surface is moveable in a lateral direction in response to rotation of the actuator about a longitudinal axis of the implant.

18. The dental implant assembly retention system as in claim 13, further comprising a spacer configured to position the implant within the container.

19. The dental implant assembly retention system as in claim 13, further comprising a spacer configured position the implant within the container such that the retention surface only contacts a collar portion of the implant.

20. A dental implant assembly retention system, comprising:

a container for the implant assembly, having at least one open end;

at least one retention surface carried by the container, the retention surface movable between a first position in which it engages a dental implant positioned within the container and a second position in which it is disengaged from the implant, to allow the implant to be removed from the container; and a spacer configured position the implant within the container such that the retention surface only contacts a collar portion of the implant.

* * * * *